(12) United States Patent
Iversen et al.

(10) Patent No.: US 11,779,473 B2
(45) Date of Patent: Oct. 10, 2023

(54) POWERED PROSTHETIC FLEXION DEVICE

(71) Applicant: Motion Control, Inc., Salt Lake City, UT (US)

(72) Inventors: Edwin K. Iversen, Salt Lake City, UT (US); Jeffrey Christensen, Sandy, UT (US); Gregory James Jacobs, Salt Lake City, UT (US)

(73) Assignee: Motion Control, Inc., Salt Lake City, UT (US)

(*) Notice: Subject to any disclaimer, the term of this patent is extended or adjusted under 35 U.S.C. 154(b) by 213 days.

(21) Appl. No.: 16/888,608

(22) Filed: May 29, 2020

(65) Prior Publication Data

US 2020/0375761 A1    Dec. 3, 2020

Related U.S. Application Data

(60) Provisional application No. 62/855,851, filed on May 31, 2019.

(51) Int. Cl.
| | |
|---|---|
| *A61F 2/58* | (2006.01) |
| *B25J 17/02* | (2006.01) |
| *A61F 2/70* | (2006.01) |
| *A61F 2/76* | (2006.01) |
| *A61F 2/72* | (2006.01) |
| *A61F 2/50* | (2006.01) |
| *A61F 2/68* | (2006.01) |

(52) U.S. Cl.
CPC ............ *A61F 2/585* (2013.01); *A61F 2/582* (2013.01); *A61F 2/72* (2013.01); *A61F 2/76* (2013.01); *B25J 17/02* (2013.01); *A61F 2002/5072* (2013.01); *A61F 2002/6836* (2013.01); *A61F 2002/6845* (2013.01); *A61F 2002/701* (2013.01); *A61F 2002/704* (2013.01); *A61F 2002/705* (2013.01); *A61F 2002/7625* (2013.01); *A61F 2002/7645* (2013.01)

(58) Field of Classification Search
CPC ...................................................... A61F 2/585
USPC .................................................... 623/61–62
See application file for complete search history.

(56) References Cited

U.S. PATENT DOCUMENTS

| | | | |
|---|---|---|---|
| 9,839,534 B2 * | 12/2017 | Lipsey | ..................... A61F 2/72 |
| 2004/0117034 A1 * | 6/2004 | Weir | ....................... A61F 2/583 623/24 |
| 2012/0286629 A1 * | 11/2012 | Johnson | ................. H02K 29/08 310/68 B |
| 2021/0025479 A1 * | 1/2021 | Maul | ......................... F16H 1/28 |
| 2021/0259856 A1 * | 8/2021 | Lince | ........................ F16H 1/32 |

* cited by examiner

*Primary Examiner* — David H Willse
(74) *Attorney, Agent, or Firm* — Thorpe North & Western LLP (57) ABSTRACT

Technology is described to provide a powered prosthetic wrist flexion device or elbow device. This device helps individuals with upper-limb loss to orient and position grasped objects.

17 Claims, 6 Drawing Sheets

POWERED PROSTHETIC FLEXION DEVICE

BACKGROUND

Prostheses (or prosthetics) are artificial devices that replace body parts (e.g., hands, arms, fingers, legs, toes). Generally, prostheses may be used to replace body parts lost by injury, disease or missing from birth.

There are thousands of individuals with absences of arms or hands in the United States alone and thousands of new amputees each year. Many of these amputees are fitted with electrically powered hand and arm prostheses. The utility of an electric hand prosthesis is greatly enhanced by the ability to rotate and flex the hand prosthesis. Once an object is grasped with a prosthetic hand, the object can be oriented for a desired task if the prosthesis can rotate and flex. A below the elbow amputee usually has four degrees of freedom available using the remnant limb, which are humeral flexion/extension, abduction/adduction, rotation and elbow flexion. To orient an object into an arbitrary orientation, two or more degrees of additional degrees of freedom are desired, which amputees may not have after an amputation. For example, simple tasks like holding a fork or a tray of food in the desired orientation can be difficult to do without wrist flexion/extension.

Wrist rotation and wrist flexion allow the amputee to better orient grasped objects. Wrist rotation alone may not be enough to provide this flexibility that most prosthesis users desire. As a result, many amputees want to utilize multiple degree-of-freedom wrists.

DETAILED DESCRIPTION

Reference will now be made to the examples illustrated in the drawings, and specific language will be used herein to describe the same. It will nevertheless be understood that no limitation of the scope of the technology is thereby intended. Alterations and further modifications of the features illustrated herein, and additional applications of the examples as illustrated herein, which would occur to one skilled in the relevant art and having possession of this disclosure are to be considered within the scope of the description.

A technology is described for a powered prosthetic wrist flexion device (PWFD) or powered elbow device for an amputee. The flexion device can be an electrically powered prosthetic wrist or elbow. This flexion device can help individuals with upper-limb loss to orient and position objects grasped by a powered hand. A powered hand may have a powered thumb with fixed fingers to enable objects to be grasped or the powered hand may have powered fingers and a powered thumb.

Figure 1:
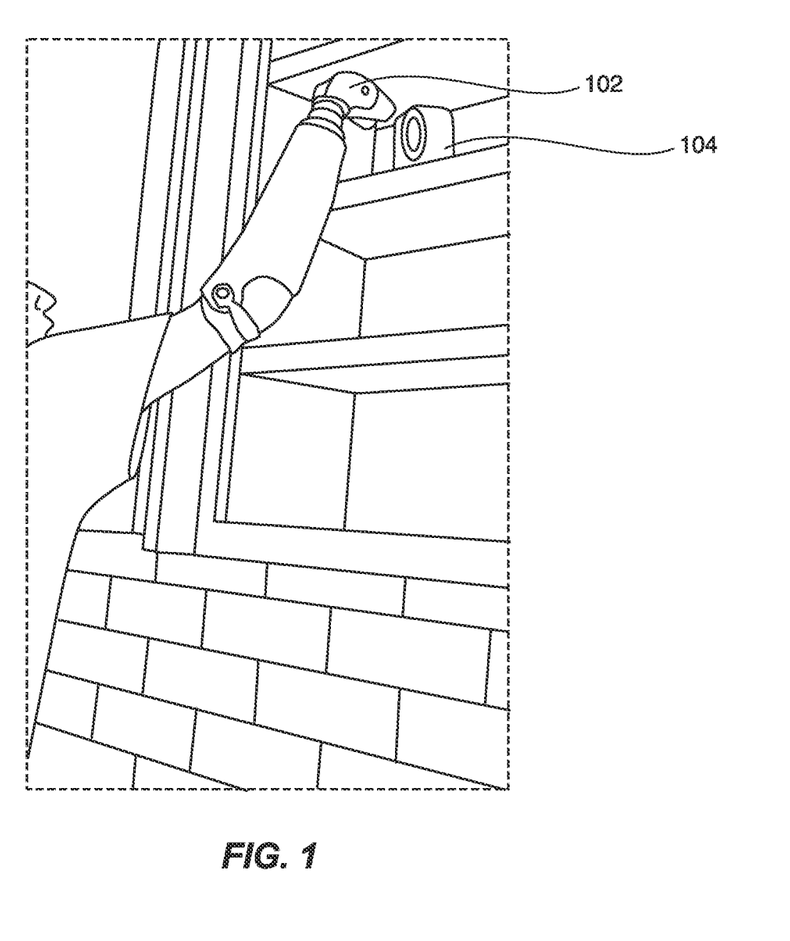
FIG. 1 illustrates an example of an individual using a wrist flexion device to reach an object on a high shelf.

FIG. 1 illustrates an individual using a powered wrist flexion device 102 to reach an object 104 on a high shelf. In FIG. 1, the flexion of the flexion device assists the prosthesis user to orient his hand to place the object on the shelf.

In order to move a grasped object from one arbitrary position and orientation to another arbitrary position and orientation, six degrees of freedom (DOFs) are desirable. Many limb deficient individuals have an intact shoulder (with 3 DOFs) and an intact elbow (one DOF) for a total of 4 intact DOFs. Without powered wrist flexion and rotation, these individuals may perform uncomfortable compensatory body motions to position and orient objects. The wrist flexion device coupled with either a passive or powered wrist rotation device can provide two additional DOFs to a limb deficient individual for a total of six DOF. Six DOFs can help an individual to position and orient objects and reduce awkward compensatory motions.

Upper-limb prosthetic devices are preferably quiet, lightweight, fast, and rugged. However, it can be difficult to assemble mechanical elements that meet these desired criteria. The elements embodied in this flexion device contribute to achieving a quiet, lightweight, fast and rugged device.

Methods for attaching the flexion device proximally to a prosthesis include, but are not limited, to the following example methods: 1) attachment to a quick disconnect, or 2) attaching the flexion device to a proximal powered wrist rotator that is fastened to a remnant arm. The quick disconnect allows for passive wrist rotation as well as the ability to interchange terminal devices (TDs). When attached proximally to a powered wrist rotator, the prosthesis is able to be actively controlled or moved passively in wrist DOFs.

The flexion device may include one or more of the following example modules: a quick disconnect (QD), a housing, a brushless direct current (DC) motor, a 3.2 to one O-ring belt drive, a two-stage friction planetary drive, a 3-tooth to 32-tooth evoloid output gear reduction, and a microcontroller. This disclosure describes a number of further aspects of the flexion device, including: the transmission, the controller, the wire routing and the enclosure.

Transmission

Figure 2:
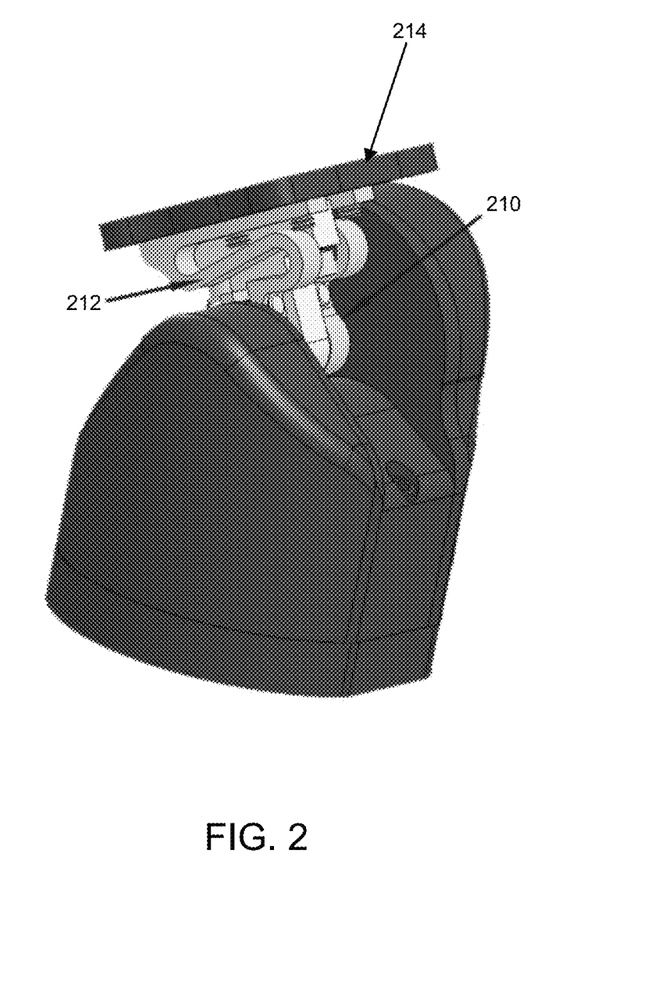
FIG. 2 illustrates an example of a series elastic element in a wrist flexion device that improves torque control and provides intrinsic compliance.
Figure 3:
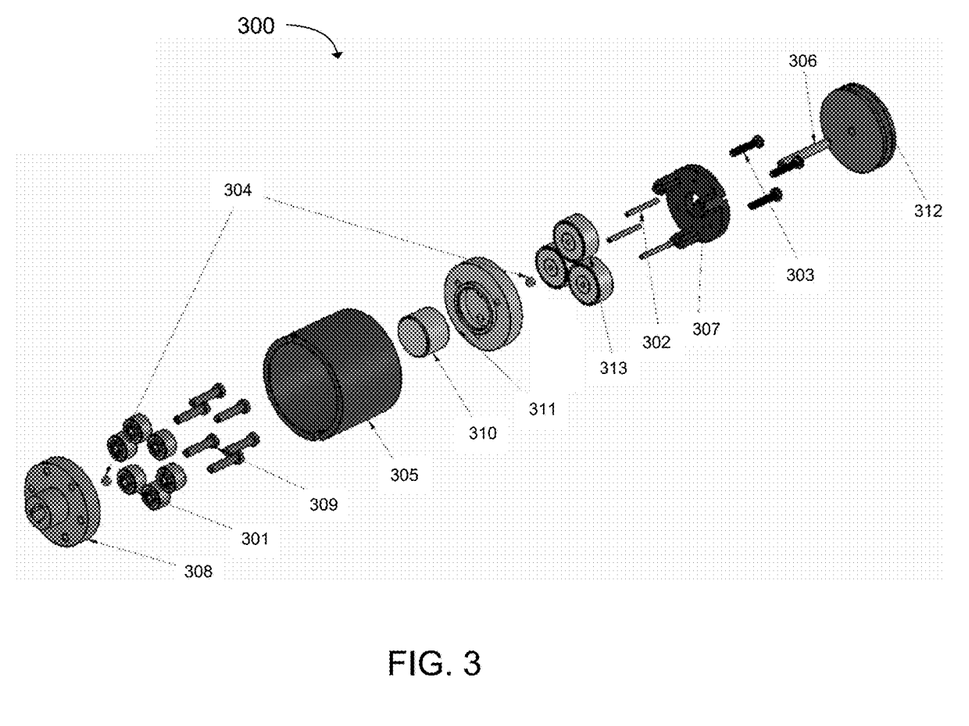
FIG. 3 illustrates an example of a two-stage friction planetary drive in an exploded view.
Figure 4:
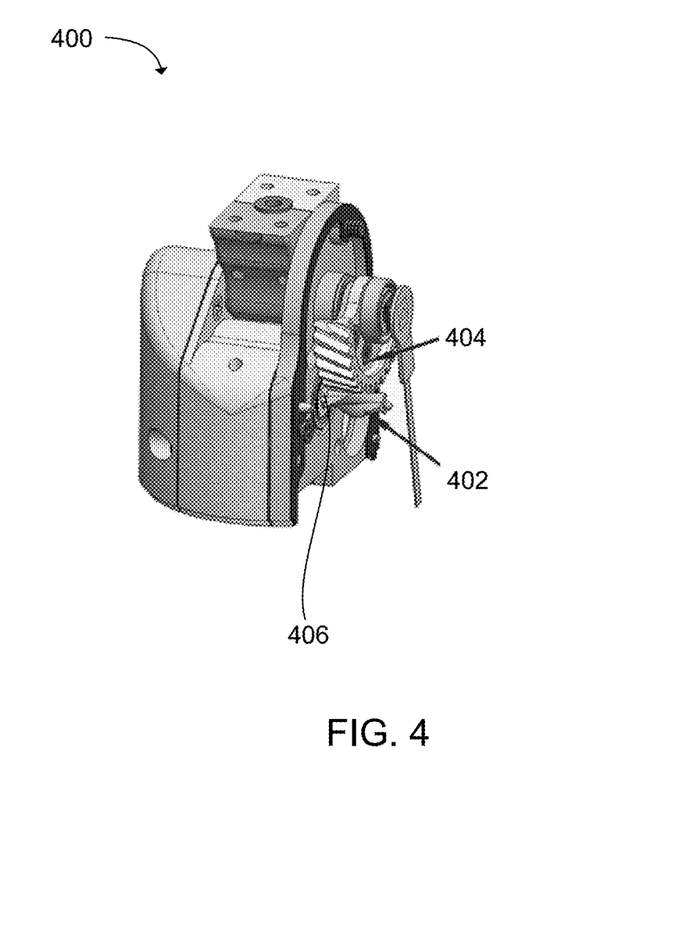
FIG. 4 illustrates an example of an output gear reduction that includes three-tooth and 32-tooth evoloid gears.

FIG. 2 illustrates that the drive train or transmission may include the following features: a break-away servo clamp 210 for overload protection and a series elastic element (SEA) 212 for improved torque control. FIG. 3 illustrates a quiet, compact, efficient two-stage friction planetary gearing 300, and FIG. 4 illustrates a compact, 3 to 32 tooth output evoloid gear drive.

The break-away servo clamp 210 is illustrated in FIG. 2 and provides protection for the amputee and/or the prosthetic device. The break-away servo clamp 210 provides overload protection and is configured to break away under a defined amount of load. When a prosthesis user overloads the hand 214 (or hand attachment interface) and the wrist, the servo clamp can slip or break free instead of breaking. Overloading may occur when an amputee falls or is pushing too hard on the terminal device. Furthermore, this break-away servo clamp 210 coupled with the SEA 212 can absorb the kinetic energy of a falling prosthesis user which can also reduce loads and potential damage to the remnant limb.

The series elastic element (SEA) 212 also helps protect an amputee and the prosthetic wrist. The SEA can provide intrinsic compliance for the drive train (FIG. 2). This intrinsic compliance helps absorb shock loads during use of the prosthesis and improves torque control. The SEA (e.g., spring) may be made from a metal such as stainless steel or another compliant metal or material. The SEA may be an S shape, may have multiple curves, may be a coil, may have sharp angles at the direction transitions (e.g., zig zag shape), may be a leaf spring, or the SEA may be any other spring type shape with a thickness of material to support wrist strain or forces on the wrist. The SEA also helps provide a smooth springy, compliant and natural feel when humans interact with the prosthetic hand and wrist. For example, when another person shakes the hand or grabs the hand.

Torque control can be improved by reducing the frequency of oscillation of the drive train. Stiff drive trains have high frequencies of oscillation. These high frequencies of oscillation may make torque control of a robotic or prosthetic joint difficult. In many cases of stiff drive trains, a motorized drive train may have a mechanical time constant at least five or more times the frequency of oscillation of drive train components. Therefore, lower stiffness drives can be more easily controlled by comparatively low frequency motors.

Because of the SEA element in the drive train of the powered flexion device, the present technology has a mechanical time constant that is lower than other drive systems. For example, this technology may have a mechanical time constant of between two and less than five due to the SEA. This lower mechanical time constant can be valuable when trying to control torque at relatively high motor frequencies. For example, the powered flexion device may exhibit low stiffness in the influence of external disturbances that would be experienced when a prosthesis user is riding a bike. In this case, the wrist may move quickly due to the SEA to maintain low stiffness and reduce loads to the remnant limb of the prosthesis user. The wrist flexion device may also include extension stop that sets a physical restriction point or stop point for the movement of the wrist structure.

FIG. 3 illustrates the two-stage friction planetary drive 300 that provides a compact gear reduction or transmission for a prosthetic flexion device. The two-stage friction planetary drive can provide gear reduction in a reduced space of a wrist and hand as compared to gearings with teeth. Space reduction is useful because the drive train and joint need to fit within the envelope of what would be otherwise be a normal human wrist and hand. Further, the two-stage friction planetary drive provides a gear reduction to volume ratio that is higher than a gearing system with teeth.

FIG. 3 illustrates a ring 305 that serves two stages of a two-stage friction planetary drive. The ring 305 or cylinder may be long or deep enough to include, contain, or act as a sleeve to both stages of the friction planetary drive. The ring 305 or cylinder may partially enclose or surround the two-stage friction planetary drive and have two open ends. The ring 305 may be mounted in an elastomeric material to reduce the noise and vibration of the drive train or transmission.

The friction planetary drive 300 has significantly less noise than a gear driven transmission. Noise is an important issue in an upper limb prosthesis because humans (e.g., amputees) use their hands to interact with other individuals and a noisy prosthetic limb can be embarrassing, distracting and create an uncanny feeling in other non-amputees.

A first set of planets 313 (e.g., the first stage) can be low friction bushings with reduced-size shafts 303, as compared to the size of the low friction bushings or planets 313. A second set of planets 301 can be low friction hubs or low friction bushings with small diameter shafts 309 or pins. The second set of planets 301 can be considered the second stage of the planetary drive. The second set of planets 301 can surround a sun roller 310, sun gear or pin for the friction planetary drive 300.

The two-stage friction planetary drive uses low friction bushings instead of rolling ball bearings that make more noise. These low friction bushings or bearings may be made of a plastic material that has damping properties and this material may help reduce the overall noise. The use of bushings also helps reduce the size of the shaft 309 used for the planet gears (e.g., the size of the shaft the low friction bushings turn on). The shaft can be made small compared to the size of the bushings which reduces friction and torque on the bushings at the bushing axis.

Two component balls 304 act as thrust washers to reduce axial friction for the planetary gears. The planets or planet gears tend to move or walk one way or the other and push on the planet assembly or planet cages made from the small shafts which pass through bushings. This movement of the planets can also push on an output 308, 311 (e.g., shaft and/or output plate) to create thrust loads in the axial direction. The component balls 304 may be located in a conical recess in the output (e.g., plate which ultimately drives the output shaft) and a ball stays in place and forms a point resistance between the planetary gears and the output (e.g., plate and shaft), and this ball can reduce the planetary gears resistance to rotation. The component balls 304 can be located adjacent to each side of the output (e.g., shaft, plate or wheel) to resist the tendency of the planet gears to move or walk and apply force on the output (plate and/or shaft).

A plate 311 or transition output may be located between the first planetary gear with the first set of planets 313 and the second planetary gear with the second set of planets 301. A cage 307 and dowels 302 may also be provided for the first set of friction planetary gears. The first set of planet gears 313 can be held in place by screws 303. In one specific example, the two-stage friction planetary drive can provide quiet, compact, efficient, back-drivable, 40:1 drive reduction. While the first stage and second stage designations have been referenced in this description for convenience, the reference to first and second stages may also be reversed.

The second set of planets 301 can drive an output 308 and this output may be an output wheel or output plate. The output 308 can also drive an output shaft (not shown here) which can slot into the output plate 308 and can drive an evoloid gear in FIG. 4.

A motor may be contained in a housing of the wrist joint. The motor may power or drive a belt drive which in turn powers or drives: a pulley 312, other input wheel or other input drive shaft mechanism. The motor can be a brushless DC motor that is mounted on O-rings to reduce noise. The motor may also be mounted in various types of elastomeric material (e.g., rubber, synthetic rubber, plastic, etc.) to reduce vibrations. A belt drive may be used to reduce noise when the motor changes direction. Alternatively, the motor may directly drive the transmission in the powered wrist. Other mechanical couplings and/or gearings between the motor and the friction planetary drive may be used to power the friction planetary drive train. In another specific example, the motors used to power the prosthetic wrist run at about 5,000 to 7,000 revolutions per minute (RPM) and the gear reductions desired are between a 500:1 up to a 1000:1 gear ratio reduction.

The two-stage planetary gearing drive train has a reduced amount of noise output because the drive train eliminates the noise created by gears with teeth. In addition, this drive train has less backlash because there is practically no gearing backlash in the absence of gear teeth. Where toothed gears have a gap in contact between the gears, the friction planetary drive does not have a gap between gears to produce backlash. For example, even if the spacing between gear teeth of a gear is only a thousandth of an inch, this is magnified by the speed of the drive and can create backlash. When that backlash reaches the end of the prosthetic hand, the hand may wobble by one tenth of an inch or even wobble up to a quarter of an inch due to the backlash. In contrast, the two-stage planetary gearing drive does not have teeth, and so there is a reduced amount of backlash in the drive train. The reduced backlash in turn eliminates wobble in the prosthetic wrist and prosthetic hand. When the motor is stopped, then a hand using toothed gears will feel very loose. Whereas, the friction planetary drive also enables the hand to move more smoothly, if another human shakes the hand or grabs the hand.

The friction planetary drive is mechanically efficient, and in the present technology, the friction planetary drive has a higher efficiency than a geared system. As a result, the friction planetary drive is back-drivable because the friction planetary drive is very efficient in the transfer of torque through the drive. The friction planetary drive is easier to back-drive because the friction planetary drive will slip and allow the hand to be back-driven. This back-drivability also results in overload protection for the wrist and the amputee. The friction planetary may provide overload protection by slipping or back driving when torques exceed the holding torque limited by the friction between the planet gears and sun rollers. For example, if a user falls on the wrist or hand, then the drive will just slip rather than breaking a gear tooth or possibly injuring the amputee's remnant limb.

There are at least three elements in the two-stage friction planetary drive that provide useful results. The first element is that the friction planetary ring 305 or cylinder is utilized as a ring for both stage one and stage two planetary drives. More specifically, the friction planetary ring is common to both stage one of the planetary gears and stage two of the planetary gears in the planetary drive. This means that there are not two rings or cylinders to be mounted within the wrist for the friction planetary drive. This common ring or cylinder improves alignment between the two friction planetary drives and speeds manufacturing. It also makes the axial direction shorter because both stages are in one ring or cylinder. For example, the axial direction may be up to 20% shorter due to the common ring 305.

The ring 305 may be mounted in an elastomeric material and this can reduce the vibrations that occur in the friction planetary and then these vibrations are not transmitted to the wrist housing. Thus, the ring is grounded via the elastomeric material to isolate and dampen the vibrations of the friction planetary drive. Removal of any teeth in the gearing also reduces vibration. Thus, a single ring can serve for isolation and dissipation (dampening) of vibrations for both stages of the friction planetary drive.

The second element is that the planets for the first planetary drive 313 utilize a relatively small hard shaft 309 to reduce friction. Since resistive torque is equal to the rubbing frictional force times the radius of the shaft, a small shaft as compared to the radius of the planets or bushings provides low friction for the planet gears.

The third element is that the small balls 304 act as thrust bearings. The thrust bearings support thrust loads in a way that produces low friction. The resisting frictional torque in the transmission is low because the resisting torque is the frictional load on the ball times a lever arm of near zero and the ball is almost a point load.

FIG. 4 illustrates a compact evoloid 3:32 gear drive 400. In one example, the compact output 3 to 32 gear stage provides a 10.6 to one gear reduction in a smaller package than hypoid gearing. These types of evoloid gears can be quiet and rugged which may make the gears useful for a prosthetic wrist application. In addition, an evoloid gear can provide a higher level of gear reduction in a smaller space than a hypoid gearing. While FIG. 4 illustrates an output gear reduction that consists of a three-tooth gear 402 and 32 tooth evoloid gear 404, other gearing ratios may be used. The evoloid gearing provides a smooth gearing transmission in a small space for the prosthetic wrist. The three-tooth gear 402 may be mounted on an output drive that exits the housing as a revolving shaft 406 which can be easily sealed from dirt, water and sound. If the output were driven using toothed gears, then sealing the gear box may be covered with a large flexible boot. In the present technology, the friction planetary gear box is sealed using the ring 305 (FIG. 3) and then the revolving shaft can be extended from both ends of the ring or cylinder for the friction planetary gear box and then sealed around only the output shaft. Evoloid gears tend to have less backlash as well.

Controller

The controller can include the following features: 1) a power-save algorithm that utilizes proximal and distal angular velocity signals, 2) hold steady motor braking and position servo braking, and 3) nested position/force servo control architecture.

The power-save process may be designed to reduce power consumption and increase battery life. Battery life is useful for the electrically powered prosthetic components in order to avoid overly frequent recharging of the wrist. The process is designed to sense the condition when the wrist flexion device or drive train is stalled when holding steady with a grasped object. This method can utilize at least three inputs: 1) motor speed using a brushless direct current (DC) motor (motor speed can be sensed by means of integrated hall effect devices), 2) motor current obtained via a current sense resistor, and 3) output velocity by means of a hall effect based position sensor.

The process can have two methods for determining when to reduce power to the motor because the motor is in a stalled state: 1) if the motor current exceeds a certain current threshold and the output velocity is below a certain amount or an output velocity threshold, then a stalled state can be detected; and 2) if the difference between motor velocity and output velocity exceeds a threshold then a stalled state can be detected. This difference can be a difference velocity threshold measured using angular velocity or rotations per time unit (e.g., rpms).

The drive train and motor may have a hold steady brake. It is valuable to allow the prosthesis user to both actively and passively position the wrist flexion device. Sometimes passively positioning the wrist flexion device is faster and more convenient and often the activity of daily living is facilitated by passively positioning a wrist, hand or elbow. For example, when the user is closing a door, the door tends to position the wrist as the wrist swings through a given arc. The hold steady braking process initiates the brake or a lock when there is no active command for a certain period of time or a predetermined period of time, which better allows for the manipulation of heavy objects. The brake or lock may be a friction brake, a pin lock, a ratcheted lock, or another type of lock. The hold steady lock can be turned on or off at will by a number of means, such as electromyographic sensors, load sensors, linear position sensors, switch input or a mobile device application.

Figure 5:
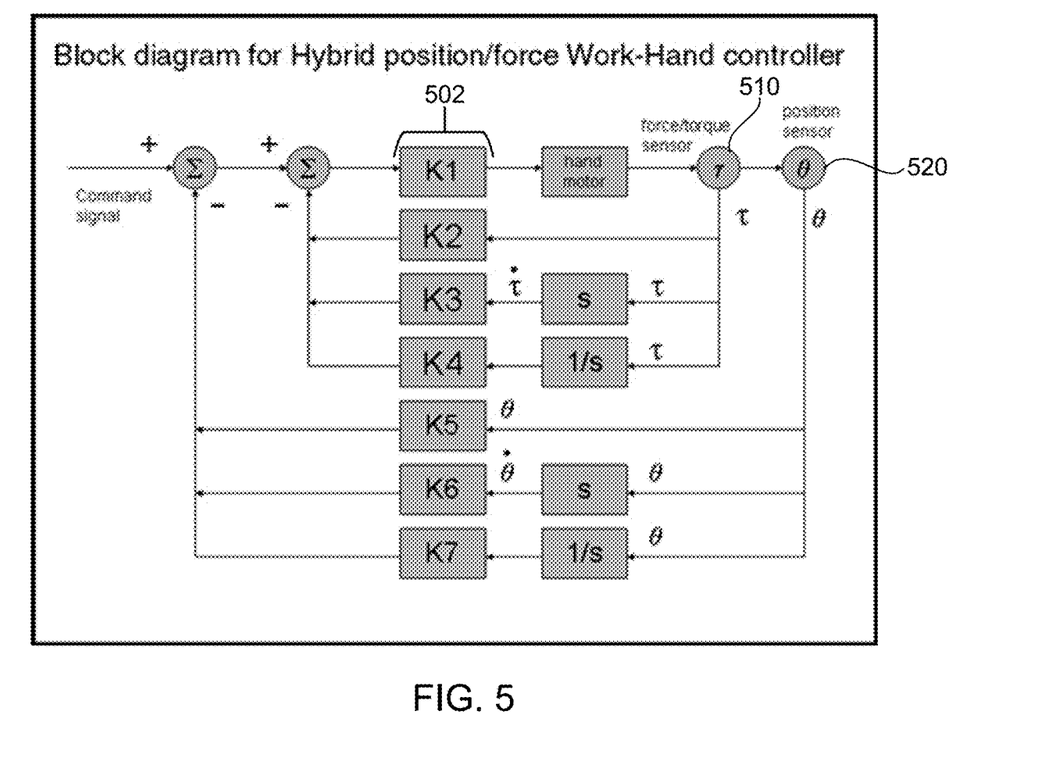
FIG. 5 is a block diagram illustrating an example of a processor or microprocessor logic for processing: command signals, a force/torque sensor signals, and/or position sensor signals of a hybrid position/force controller.

This device may also include a position and force hybrid controller. The servo control method utilized in the wrist flexion device is a force/position hybrid closed loop system (as illustrated in FIG. 5). This system can allow the wrist flexion device to be controlled with precise position control or high-fidelity force control. By strategically commanding the gains K1-K7 502, the behavior of the wrist can have varied stiffness or precise positional accuracy.

FIG. 5 is a block diagram illustrating the processing of command signals that include force/torque sensor signals 510, and position sensor signals 520 of the hybrid position/force controller(s). The wrist flexion device can have a stronger braking behavior by implementing a position servo for which the desired position is the hold steady position. This braking behavior of the motor and drive train can be initiated with a bump switch in or on the wrist device, an electromyographic (EMG) co-contraction of an amputee's muscle or an even longer hold steady period of time. The wrist flexion device can be controlled to exhibit active compliance through use of a hybrid position and force controller.

Figure 6:
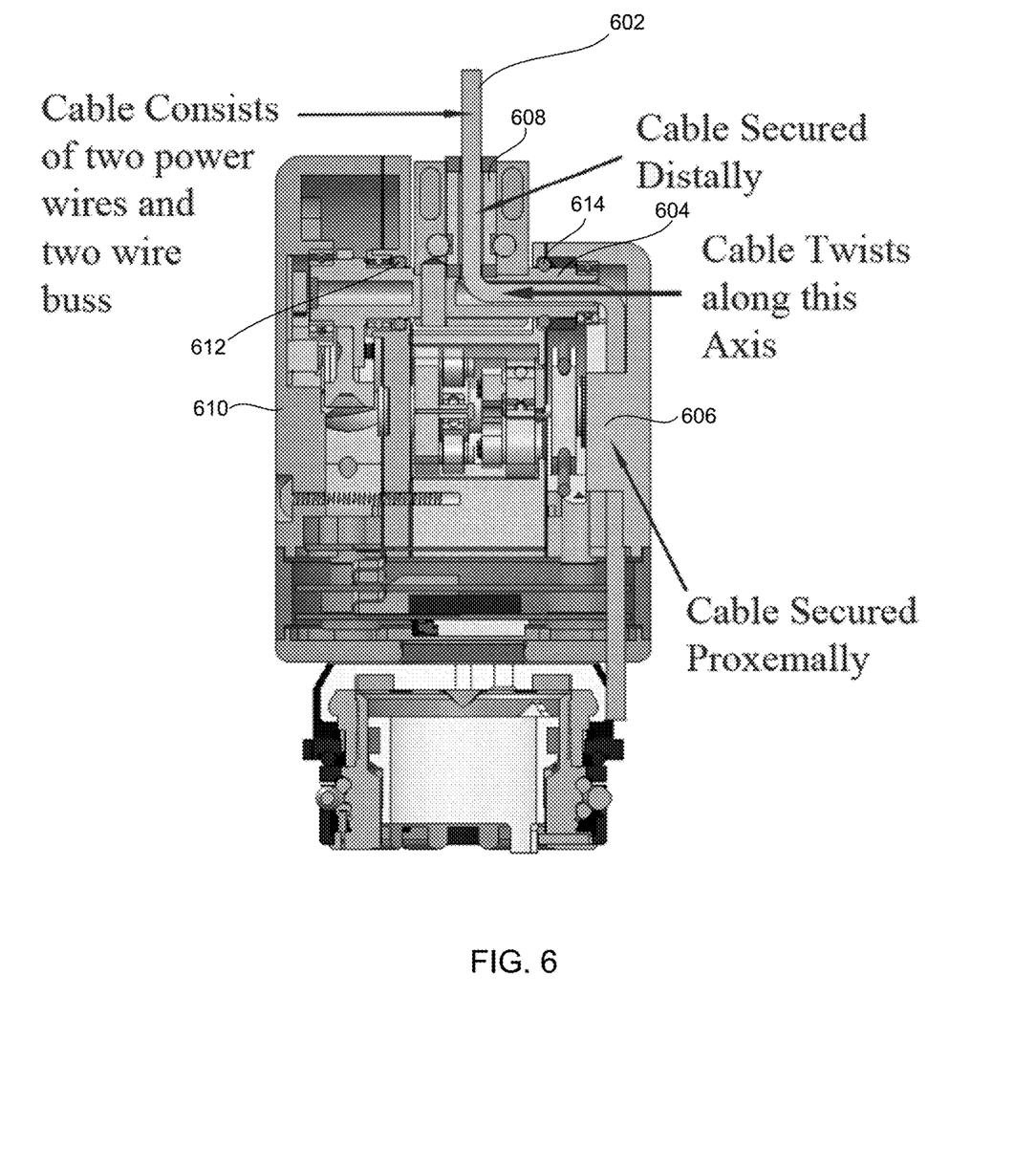
FIG. 6 illustrates that the wire routing of the wrist flexion device enables the power and control two wire bus to make up a cable that is routed via a hole or channel in the output drive shaft.

FIG. 6 illustrates that the wire routing of the wrist flexion device enables the power and control two wire bus 602 to form a cable to be routed down a hole and/or axial channel formed in the output drive shaft 604. This allows a cable to twist along a cable axis to increase the wire's operational period or wire life, eliminates bending of the cables, and replaces a bending motion with a twisting motion distributed along a length of the cable in the hollow shaft. The stress on the conductors can be reduced and wire life or operational time period is increased. FIG. 6 further illustrates the cable routing through the wrist flexion device, where the cable can be clamped proximally 606 and distally 608 allowing the cable to twist along the axis of wrist flexion. This further minimizes stress on wires and increases cycle life and durability of the system.

The wrist flexion device enclosure 610 provides protection from dirt and water, encapsulates sound, and allows for an extended range of motion. This is accomplished by configuring the housing in two places 612, 614 on either end of the output drive such that the moving seals or seals for moving parts are limited to the rotary shafts that are relatively easy to seal. Furthermore, the housings are sandwiched with gaskets to seal for dirt and water and to isolate and dissipate noise.

Even though this technology described above refers to a wrist, the same technology can be used in any type of prosthetic or robotic limb flexion device. For example, this technology can be used on an elbow or similar prosthetic joint where flexing is useful. In addition, the flexion device may be used in a prosthetic device for ulnar and radial deviation.

Furthermore, the described features, structures, or characteristics may be combined in any suitable manner in one or more examples. In the preceding description, numerous specific details were provided, such as examples of various configurations to provide a thorough understanding of examples of the described technology. One skilled in the relevant art will recognize, however, that the technology can be practiced without one or more of the specific details, or with other methods, components, devices, etc. In other instances, well-known structures or operations are not shown or described in detail to avoid obscuring aspects of the technology.

Although the subject matter has been described in language specific to structural features and/or operations, it is to be understood that the subject matter defined in the appended claims is not necessarily limited to the specific features and operations described above. Rather, the specific features and acts described above are disclosed as example forms of implementing the claims. Numerous modifications and alternative arrangements can be devised without departing from the spirit and scope of the described technology.

The invention claimed is:

1. An electrically powered prosthetic joint, comprising:
a housing to contain a prosthetic joint for an amputee;
a motor attached to the housing;
a two-stage friction planetary drive having planet gears that are bushings, that is powered by the motor;
a ring of the two-stage friction planetary drive that is common to a first stage and a second stage of the two-stage friction planetary drive;
an output drive shaft driven by the two-stage friction planetary drive, wherein the output drive shaft moves a prosthetic wrist joint; and
a series elastic element to reduce stiffness and frequency in a drive train to provide high frequency motor control and torque control.

2. The electrically powered prosthetic joint as in claim 1, wherein the two-stage friction planetary drive includes planet gears that are low friction bushings with reduced size shafts as compared to a size of the low friction bushings, a sun gear that is a pin and the ring is a cylinder bushing.

3. The electrically powered prosthetic joint as in claim 1, further comprising ball bearings for the first stage and second stage of planet gears to act as thrust bearings.

4. The electrically powered prosthetic joint as in claim 1, further comprising a motor controller utilizing a power save process that senses stall through monitoring distal and proximal motor position or angular velocity.

5. The electrically powered prosthetic joint as in claim 1, wherein the motor is a brushless DC motor that is mounted on O-rings.

6. The electrically powered prosthetic joint as in claim 1 that is controlled to exhibit active compliance through use of a hybrid position and force controller.

7. The electrically powered prosthetic joint as in claim 1, further comprising a controller that senses stall of the motor through monitoring stall current and reduces power to the motor when stalling occurs.

8. The electrically powered prosthetic joint as in claim 1, further comprising an extension stop.

9. The electrically powered prosthetic joint as in claim 1, further comprising an output drive that exits the housing as a revolving shaft, wherein the revolving shaft is sealed for dirt, water and sound.

10. An electrically powered prosthetic joint, comprising:
a housing to provide a prosthetic joint for an amputee;
a motor attached to the housing;
a two-stage friction planetary drive having planetary gears that are bushings, that is powered by the motor;
a ring around the two-stage friction planetary drive that is common to a first stage and a second stage of the two-stage friction planetary drive, wherein the two-stage friction planetary drive includes planet gears with low friction bushings with reduced size shafts as compared to a size of the low friction bushings;
an output drive shaft driven by the two-stage friction planetary drive, wherein the output drive shaft moves a prosthetic wrist; and
a series elastic element coupled to the output drive shaft to reduce stiffness and frequency in a drive train and to provide high frequency torque control.

11. The electrically powered prosthetic joint as in claim 10, further comprising ball bearings in the first stage and second stage to act as thrust bearings.

12. The electrically powered prosthetic joint as in claim 10, further comprising a servo clamp on the output drive shaft that is configured to break away under a defined amount of load to act as overload protection.

13. The electrically powered prosthetic joint as in claim 10, wherein the motor is a brushless DC motor that is mounted on O-rings.

14. An electrically powered prosthetic joint, comprising:
a housing to contain a prosthetic joint for an amputee;
a motor attached to the housing;
a two-stage friction planetary drive having planet gears that are bushings, that is powered by the motor;
a ring of the two-stage friction planetary drive that is common to a first stage and a second stage of the two-stage friction planetary drive; and
an output drive shaft driven by the two-stage friction planetary drive, wherein the output drive shaft moves a prosthetic wrist joint; and
a servo clamp on the output drive shaft, which is configured to break away under a defined amount of load and to act as overload protection for an amputee's remnant limb.

15. The electrically powered prosthetic joint as in claim 14, further comprising ball bearings for the first stage and second stage of planet gears to act as thrust bearings.

16. An electrically powered prosthetic joint, comprising:
a housing to contain a prosthetic joint for an amputee;
a motor attached to the housing;
a two-stage friction planetary drive having planet gears that are bushings, that is powered by the motor;
a ring of the two-stage friction planetary drive that is common to a first stage and a second stage of the two-stage friction planetary drive;
an output drive shaft driven by the two-stage friction planetary drive, wherein the output drive shaft moves a prosthetic wrist joint; and
a cable that passes through the housing and is routed along an axial channel formed in the output drive shaft, wherein the cable twists along a cable axis to increase wire operational period.

17. An electrically powered prosthetic joint, comprising:
a housing to contain a prosthetic joint for an amputee;
a motor attached to the housing;
a two-stage friction planetary drive having planet gears that are bushings, that is powered by the motor;
a ring of the two-stage friction planetary drive that is common to a first stage and a second stage of the two-stage friction planetary drive;
an output drive shaft driven by the two-stage friction planetary drive, wherein the output drive shaft moves a prosthetic wrist joint; and
output evoloid gears coupled to the output drive shaft, wherein the output evoloid gears reduce a size and noise of a gearing.

\* \* \* \* \*